United States Patent [19]

Goudie

[11] 4,303,674
[45] Dec. 1, 1981

[54] SUBSTITUTED DECALINS, THEIR PREPARATION AND USE

[75] Inventor: Alexander C. Goudie, Harlow, England

[73] Assignee: Beecham Group Limited, England

[21] Appl. No.: 153,077

[22] Filed: May 27, 1980

[30] Foreign Application Priority Data

Jun. 8, 1979 [GB] United Kingdom ............... 20052/79
Oct. 29, 1979 [GB] United Kingdom ............... 37457/79

[51] Int. Cl.³ ..................... A61K 31/12; C07C 49/637
[52] U.S. Cl. .................................... 424/331; 568/374; 568/347; 260/340.7; 260/340.9 R
[58] Field of Search ........................ 568/374; 424/331; 260/340.7, 340.9 R

[56] References Cited

U.S. PATENT DOCUMENTS 2,614,123 10/1952 Neuman et al. ..................... 568/374
3,565,356 4/1970 Salloy ................................. 568/374

FOREIGN PATENT DOCUMENTS 1213399 3/1966 Fed. Rep. of Germany ...... 568/374

OTHER PUBLICATIONS

Judoy, Chem. Abst., vol. 63 #11386b (1965).
Judoy, et al. Chem. Abst., vol. 69 #35508y (1968).
McOmee, Protective Groups in Organic Synthesis, pp. 325-331 (1976).

Primary Examiner—Natalie Trousof
Assistant Examiner—James H. Reamer
Attorney, Agent, or Firm—Jacobs & Jacobs

[57] ABSTRACT

A compound of formula (I):

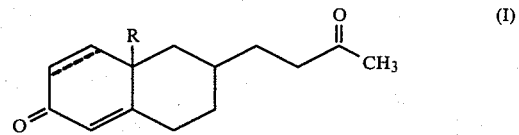

wherein the dotted line indicates an optional double bond and R is a hydrogen atom or a methyl group has topical anti-inflammatory activity.

5 Claims, No Drawings

SUBSTITUTED DECALINS, THEIR PREPARATION AND USE

This invention relates to substituted decalins, their preparation and use.

Topical anti-inflammatories are of use in the treatment of a large number of inflammatory skin conditions and inflammatory conditions of the eyes, ears, nose and throat. Most topical anti-inflammatories used to date are steroids. These compounds have proven to be very effective but they tend to have a number of side effects. Many physicians consider these side effects so serious as to severely limit the applicability of the steroids. Clearly it would be desirable to find topical anti-inflammatory agents that were free of steroidal side effects.

The present invention provides the compounds of the formula (I):

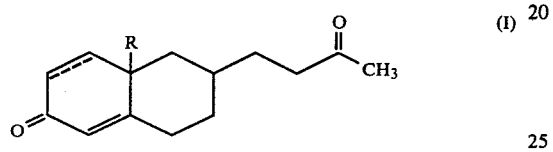

wherein the dotted line indicates an optional double bond and R is a hydrogen atom or a methyl group.

Aptly R is a methyl group. Aptly R is a hydrogen atom.

The compounds of the formula (I) may have the α- and β- configuration at the point of attachment of the side chain. The invention extends of course to each of these isomers, and also to mixtures thereof.

(When used herein α means trans in regard to the R group, β means cis in regard to the R group.)

It is a surprising feature of the compounds of this invention that they exhibit anti-inflammatory activity when applied topically but do not appear to be effective anti-inflammatory agents when administered orally.

The present invention provides a pharmaceutical composition adapted for topical administration which comprises a compound of the formula (I) and a pharmaceutically acceptable carrier therefor.

The compounds of the invention will normally be made up into a cream, gel or ointment for topical administration to the skin comprising a compound of the formula (I) which has been formulated as a cream, gel or ointment.

Cream, gel or ointment formulations that may be used for compounds of the formula (I) are conventional formulations well known in the art, for example, as described in standard text books of pharmaceutics cosmetics, such as Harry's Cosmeticology published by Leonard Hill Books, and the British Pharmacopoeia. A standard emulsifying ointment base or an anhydrous polyethylene glycol are simple examples of such suitable formulations.

The compositions of this invention may be used in the topical treatment of atopic and contact dermititis, psoriasis, eczema and other inflammatory dermatoses and in inflammatory conditions of eyes, ears, nose and throat.

It will be appreciated that the amount of the compound of the formula (I) used will depend on a number of factors such as the nature and severity of the disorder being treated, and the specific compound being used. However by way of illustration it is believed that effective therapy can be achieved using roughly similar amounts of the compounds of formula (I) as would be used of hydrocortisone.

The compositions of this invention may also contain other therapeutic agents such as anti-infective agents. Suitable anti-infective agents include the topically applicable antibacterial and anti-fungal agents already in use in topical anti-inflammatory preparations.

The present invention also provides a process for the preparation of a compound of the formula (I), which process comprises the de-protection of a compound of formula (II) or (III):

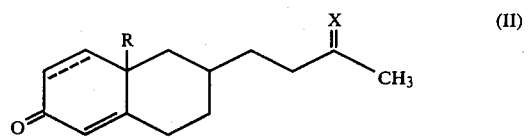

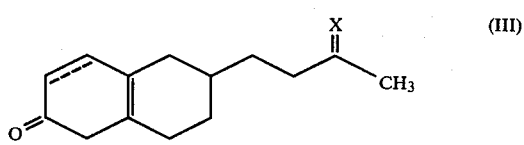

wherein X is a protected carbonyl group.

Suitable examples of protected carbonyl groups X include diethyl ether, and ketals such as ethyllene dioxy and propylene dioxy. Preferably X is ethylene dioxy.

The de-protection reaction may be carried out in any convenient manner, depending on the nature of the group X. By way of example with X as ethylene dioxy acid hydrolysis is suitable.

The preparation of compounds of the formula (II) and (III) may simply be illustrated in the following flow diagrams, in which for clarity X is illustrated as ethylene dioxy. The conversion of a compound of formula (II) or (III) not containing the optical double bond into the corresponding compound containing the optional double bond may simply be carried out by oxidation. A suitable oxidising agent to use is 2,3-dichloro-5,6-dicyano-1,4-benzoquinone.

Synthetic Route 1

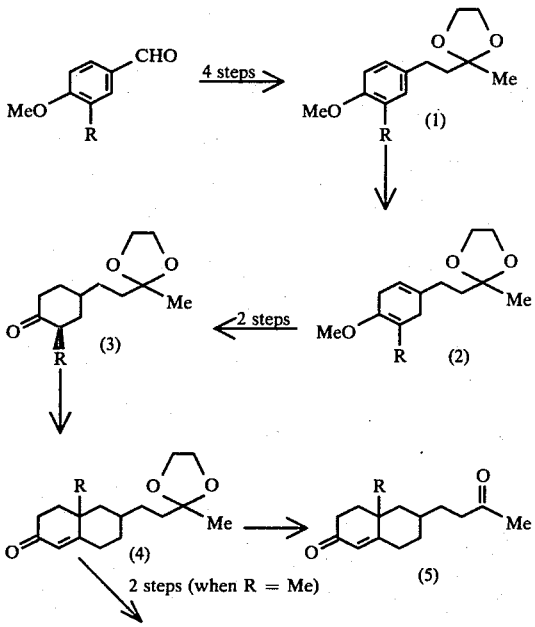

-continued
Synthetic Route 1

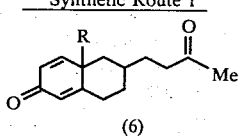

Synthetic Route 2

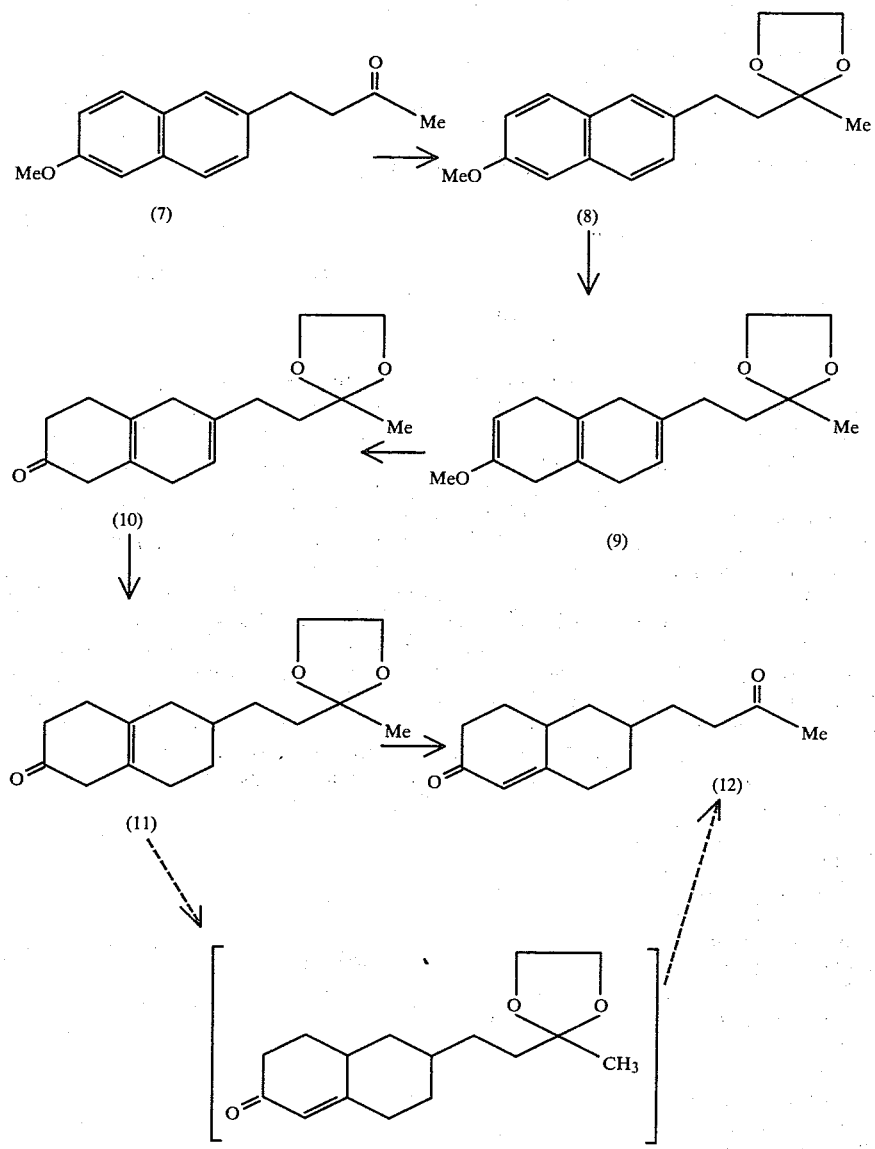

reflux for 24 hours with constant removal of water using a Dean-Stark trap. After cooling the resulting solution was washed with dilute aqueous sodium bicarbonate solution and then water, dried ($Na_2SO_4$) and concentrated to give a viscous, yellow oil (83.3 g).

This crude product was dissolved in ethanol (2×500 ml) and hydrogenated at room temperature and pressure for 3 hours using 10% palladium on charcoal (2×5 g) as catalyst. After removal of the catalyst by filtration, a solution of 5 N hydrochloric acid (400 ml) was added and the resulting mixture heated overnight at reflux. After cooling and removal of most of the ethanol, the crude product was extracted into diethyl ether (3×250 ml) and this in turn was washed with water (2×100 ml), dried ($Na_2SO_4$) and concentrated to afford 4-(4-methoxy-3-methylphenyl)butan-2-one (54.2 g) as a dark yellow oil.

A mixture of the latter (54.2 g), ethylene glycol (180 ml), p-toluenesulphonic acid (1.7 g) and benzene (400

From the foregoing, it will be appreciated that certain important intermediates are of the formula (II) and (III) as defined. These compounds form part of this invention.

The following Examples are illustrative of this invention.

EXAMPLE 1

2-[2-(4-methoxy-3-methylphenyl)ethyl]-2-methyl-1,3-dioxolane (1)

A mixture of 4-methoxy-3-methylbenzaldehyde (50 g), ethyl acetoacetate (50 ml), piperidine (3.5 ml), phenylacetic acid (1 g) and benzene (500 ml) was heated at ml) was heated for 2 days at reflux with constant removal of water as before. The resulting solution was cooled and the benzene layer removed. The glycol layer was basified with dilute aqueous sodium bicarbonate solution and extracted with ether (2×250 ml). The combined organic layers were then washed with water, dried ($Na_2SO_4$) and concentrated to give 2-[2-(4-methoxy-3-methylphenyl)ethyl]-2-methyl-1,3-dioxolane (63.7 g: 81% overall yield) as a dark yellow oil.

N.M.R. ($CDCl_3$) δ 7.10–6.60 (3H, m), 3.94 (4H, s), 3.77 (3H, s), 2.95–2.50 (2H, m), 2.19 (3H, s), 2.10–1.65 (2H, m) and 1.35 (3H, s).

EXAMPLE 2

4-(3′,3′-Ethylenedioxybutyl)-1-methoxy-2-methyl cyclohexa-1,4-diene (2)

A solution of the above dioxolane (11.8 g) in diethyl ether (40 ml) and liquid ammonia (160 ml) was treated over 10 minutes with 10 pieces of lithium (2.56 g) with constant stirring. After a further 15 minutes isopropanol (30 mls) was added cautiously over a period of 15 minutes. The resulting solution was then stirred for 5 hours until the blue colouration disappeared and then allowed to stand overnight at room temperature. The mixture was next diluted with water (150 ml) and diethyl ether (250 ml) and the ethereal layer was then washed with water (2×100 ml), dried ($Na_2SO_4$) and concentrated to give a colourless oil (11.5 g: 97%).

N.M.R. ($CDCl_3$) δ 5.50–5.15 (1H, m), 3.83 (4H, s), 3.43 (3H, s), 2.90–2.50 (4H, m), 2.20–1.50 (4H, m), 1.57 (3H, broad s) and 1.22 (3H, s).

EXAMPLE 3

4-(3′,3′-Ethylenedioxybutyl)-2-methyl cyclohexanone (3)

A solution of the above diene (21.3 g) in methanol (1220 ml) and water (244 ml) containing oxalic acid (18.3 g) was stirred at room temperature for 1 hour before being treated with a solution of sodium hydroxide (12.2 g) in water (50 ml). After removing most of the methanol the residue was extracted with diethyl ether (3×250 ml). The organic extracts were washed with dilute aqueous sodium bicarbonate, dried ($K_2CO_3$) and concentrated to give a colourless oil (17.07 g).

Hydrogenation of the latter in ethyl acetate (500 ml) took 5 hours at room temperature and pressure using 10% palladium on charcoal (1.7 g). After removal of the catalyst and solvent, the crude product was purified by column chromatography on alumina using gradually increasing concentrations of diethyl ether in 60°–80° petrol to afford 4-(3′,3′-ethylenedioxybutyl)-2-methyl cyclohexanone (7.0 g: 31%) b.p. 123°–4°/0.45 mm.

N.M.R. ($CDCl_3$) δ 3.90 (4H, s), 2.9–1.0 (12H, m), 1.23 (3H, s) and 0.95 (3H, d, J=6 c.p.s.).

EXAMPLE 4

6-(3′,3′-Ethylenedioxybutyl)-4a-methyl-2,3,4,4a,5,6,7,8-octahydro-2-naphthalenone (4)

To an efficiently stirred mixture of the above cyclohexanone (3 g) and 3 N ethanolic sodium ethoxide solution (0.18 ml) at −10° under nitrogen was added dropwise methyl vinyl ketone (1.15 ml) over 7 hours. The reaction mixture was allowed to stand at −10° overnight and the cold mass was then transferred with diethyl ether and brine to a separatory funnel and extracted with diethyl ether (3×100 ml). The combined extracts were washed with saturated brine and concentrated to leave a clear oil which was then taken up in ethanol (100 ml) and refluxed with a 10% sodium hydroxide solution (25 ml) for 50 minutes. After cooling and removal of most of the ethanol the residue was extracted into diethyl ether (3×100 ml) and ethereal extracts washed with water, dried ($Na_2SO_4$) and concentrated. The crude product was purified by column chromatography on alumina using increasing concentrations (0–20%) of ether in hexane as eluant to give pure starting cyclohexanone (0.73 g) and then 6-(3′,3′-ethylenedioxybutyl)-4a-methyl-2,3,4,4a,5,6,7,8-octahydro-2-naphthalenone (1.55 g: 56% based on recovered starting cyclohexanone) as a clear oil.

N.M.R. ($CDCl_3$) δ 5.75 (1H, broad s), 3.94 (4H, s), 2.7–1.2 (15H, m), 1.30 (3H, s) and 1.24 (3H, s).

EXAMPLE 5

4a-Methyl-6-(3′-oxobutyl)-2,3,4,4a,5,6,7,8-octahydro-2-naphthalenone (5)

A solution of the above octahydro-2-naphthalenone (4) (1.25 g) in acetic acid (30 ml) and 1 N sulphuric acid (35 ml) was heated on a steam bath for 1 hour before being cooled and extracted with diethyl ether (3×100 ml) the ethereal extracts were washed with dilute aqueous sodium hydroxide solution and then water, dried ($Na_2SO_4$), and concentrated to afford 4a-methyl-6-(3′-oxobutyl)2,3,4,4a,5,6,7,8-octahydro-2-naphthalenone (0.89 g: 85%) as a colourless oil.

N.M.R. ($CDCl_3$) δ 5.75 (1H, broad s), 2.8–1.1 (15H, m), 2.14 (3H, s) and 1.25 (3H, s).

EXAMPLE 6

4a-Methyl-6-(3′-oxobutyl)-2,4,5,6,7,8-hexahydro-2-naphthalenone (6)

A mixture of 6-(3′,3′-ethylenedioxybutyl)-4a-methyl-2,3,4,4a,5,6,7,8-octahydro-2-naphthalenone (1.25 g) and 2,3-dichloro-5,6-dicyano-1,4-benzoquinone (1.02 g) was heated in refluxing dioxane (100 ml) for 24 hours under nitrogen. The resulting solution was cooled and diluted with diethyl ether (20 ml). The white precipitate which formed was removed by filtration before concentrating the mixture. The crude product was then treated in exactly the same way as the previous preparation to afford a mixture of firstly 4a-methyl-6-(3′-oxobutyl)-2,3,4,4a,5,6,7,8-octahydro-2-naphthalenone (0.33 g: 32%) and secondly 4a-methyl-6-(3′-oxobutyl)-2,4,5,6,7,8-hexahydro-2-naphthalenone (6).

N.M.R. ($CDCl_3$) δ 6.77 (1H, d, J=10 c.p.s.), 6.25–5.92 (1H, m), 6.02 (1H, broad s), 2.70–1.20 (11H, m), 2.14 (3H, s) and 1.33, 1.26 (3H overall, 2 singlets).

EXAMPLE 7

2-(3′-Oxobutyl)-6-methoxynaphthalene (7) may be prepared in the manner described in UK Pat. No. 1,474,377.

EXAMPLE 8

2-(3′,3′-Ethylenedioxybutyl)-6-methoxynaphthalene (8)

2-(3′-Oxobutyl)-6-methoxynaphthalene (7) (100 g) ethylene glycol (350 ml) and benzene (1000 ml) were azeotropically refluxed with a catalytic amount of p-toluenesulphonic acid (2.5 g) for 2 days. The solution was cooled, basified with sodium bicarbonate solution and extracted with ether. The combined organic phases were dried over magnesium sulphate, filtered and evaporated to give the product as a white crystalline solid which was recrystallised from pet ether (60°–80° C.) to yield the desired pure title compound (8) (85.1 g: 71%) NMR (60 MHz)τ2.3–3.0 (6H, multiplet), 6.0 (4H, singlet), 6.1 (3H, singlet), 7.0–7.3 (2H, multiplet), 7.8–8.1 (2H, multiplet), 8.6 (3H, singlet).

EXAMPLE 9

2-(3',3'-Ethylenedioxybutyl)-6-methoxy-1,4,5,8-tetrahydronaphthalene (9)

2-(3',3'-Ethylenedioxybutyl)-6-methoxynaphthalene (8) (9.52 g) in a mixture of tetrahydrofuran (150 ml) and ethanol (150 ml) was added through a dropping funnel to liquid ammonia (300 ml). Sodium (13.8 g), 0.6 g-atom) was then added in small pieces over a 15 minute period, after which time the colourless solution finally turned blue. The reaction mixture was allowed to stir until the blue colour disappeared and then the ammonia was allowed to evaporate overnight. Water was added to the residue and then tetrahydrofuran and ethanol were removed under vacuum. The solution was further diluted with water, extracted with chloroform. The organic phases were dried over sodium sulphate, filtered and evaporated to give a yellow solid which was recrystallised from methanol yielding (9) as a white solid (9.2 g; 95%) m.pt. 58°–59° C. NMR (60 MHz) τ: 4.6 (1H, broad singlet), 5.4 (1H, broad singlet), 6.1 (4H, singlet), 6.5 (3H, singlet), 7.3–8.4 (12H, multiplet), 8.7 (3H, singlet).

EXAMPLE 10

6-(3',3'-Ethylenedioxybutyl)-1,2,3,4,5,6,7,8-hexahydronaphthalene-2-one (10)

2-(3',3'-Ethylenedioxybutyl)-6-methoxy-1,4,5,8-tetrahydronaphthalene (9) (9.0 g) was stirred at room temperature in a solution containing oxalic acid (6.64 g, 0.074 mole) in methanol (444 ml) and water (90 ml). Sodium bicarbonate solution was added after 40 minutes. Methanol was removed under vacuum and the aqueous layer was extracted with chloroform. The organic phase was dried over sodium sulphate, filtered and evaporated to give (10) as a sweet-smelling yellow oil (7.76 g: 91%) IR 1720 cm$^{-1}$ NMR (60 M Hz)τ: 4.6 (1H, broad singlet), 6.1 (4H, singlet) 6.8–8.3 (14H, multiplet), 8.65 (3H, singlet).

EXAMPLE 12

6-(3'-Oxobutyl)-2,3,4,4a,5,6,7,8-octahydronaphthalene-2-one (12)

6-(3',3'-Ethylenedioxybutyl)-1,2,3,4,5,6,7,8-hexahydronaphthalene-2-one (10) (2 g) was hydrogenated in benzene/ethanol (1:1) using tris-(triphenylphosphine)rhodium chloride (0.4 g) as catalyst over 2 days. The solution was concentrated under vacuum. The residue (which contained (11)) was redissolved in chloroform and stirred overnight at room temperature with 5 N hydrochloric acid. The aqueous phase was extracted with chloroform. The combined organic phases were dried over magnesium sulphate, filtered and evaporated to give a viscous yellow oil. This was purified by column chromatography on silica gel eluting with diethyl ether. The desired product (12) was obtained as a yellow liquid (0.83 g). IR 1720, 1685 cm$^{-1}$. NMR (60 M Hz)τ: 4.2 (1H, broad singlet), 7.9 (3H, singlet), 7.4–8.7 (16 H, multiplet). It is believed the product is mainly the α-isomer.

PHARMACOLOGICAL DATA SECTION

1. Compounds (5) and (6) were tested for anti-inflammatory activity in a topical model based on that described by Fregnan G. B. & Torsello, A. L. (1975) Current Therapeutic Research 17, No. 4, 375–381.

In the test the activity of the novel compounds was compared with that of naproxen. In outline the method is as follows:

Rats, Charles River Wistar strain, ♂ 10/group. Weight range 220–260 g.

Irritant solution applied consists of 74% diethyl ether (20% pyridine, 5% dist. H$_2$O, 1% croton oil. 0.05 ml is placed on each ear, compound being included in the irritant solution on one ear. 6 hours later the ears are removed by cutting along the hairline and weighed.

—ve controls—no irritant solution.

+ve controls—irritant solution on both ears.

In the test compound (5) significantly reduced the increase in ear weight brought about by the irritant solution. The activity was at the same dose as that of naproxen. Compound (6) was tested in this test and appeared equi-active with Compound (5).

|  | Mean weight of Treated Ear m.g. | Mean weight of Untreated Ear m.g. |
|---|---|---|
| —ve control | 128.4 ± 2.0 | 122.5 ± 1.9 |
| +ve control | 163.2 ± 6.7 | 151.8 ± 6.4 |
| Compound (5) 2 mg/rat | **135.4 ± 3.3 (80%) | 169.0 ± 7.4 (−59%) |
| Compound (6) 2 mg/rat | ***134.3 ± 2.3 (83%) | 159.1 ± 5.1 (−25%) |
| Naproxen 2 mg/rat | **139.5 ± 3.0 (68%) | 162.2 ± 4.9 (−35%) |

***p < 0.001 Difference from +ve control
**P < 0.01 Students 't'

Using the above procedure the following results were obtained for compound (12):

|  | Mean weight of Treated Ear m.g. | Mean weight of Untreated Ear m.g. |
|---|---|---|
| —ve control | 127.0 ± 3.1 | 130.1 ± 3.3 |
| +ve control | 152.2 ± 4.8 | 159.4 ± 4.2 |
| Compound (12) (4 mg/rat) | *136.9 ± 2.9 (61%) | 148.0 ± 3.9 (51%) |
| Naproxen (2mg/rat) | 141.2 ± 3.7 (44%) | 155.9 ± 4.1 (12%) |

*p < 0.05 on students 't'

2. Activity of Compound (5) in an anti-inflammatory test induced by the application of cantharidin to the rat ear This model developed by Boris A and Hurley M., (1977) J. Invest. Dermatology, 68, 161–164 is claimed to be selective for the anti-inflammatory activity of corticosteroids. Groups of ten male Wistar rats received 0.05 ml per ear of a solution of 400 μg of cantharidin plus or minus compound in tetrahydrofuran. A time course of inflammation showed that no increase in weight occurred for the first 24 hours but at 48 hours a consistent increase in weight gain occurred. Compound (5) was compared with naproxen and hydrocortisone and the results are shown below.

| Group | Treated Ear Wt mg ± s.e. | % Inhibition | Untreated Ear Wt mg ± s.e. | % Inhibition |
|---|---|---|---|---|
| Normal control | 95.0 |  | 92.9 |  |

-continued

| Group | Treated Ear Wt mg ± s.e. | % Inhibition | Untreated Ear Wt mg ± s.e. | % Inhibition |
|---|---|---|---|---|
| Inflamed control | 162.0 | | 146.3 | |
| Compound (5) 4 mg/ear | *140.5 | 32 | 134.3 | 22 |
| Naproxen 4mg/ear | 184.8 | −34 | 145.0 | 2 |
| Hydrocortisone 2 mg/ear | **133.1 | 43 | 142.0 | 8 |

Significantly different from the inflamed control assessed by the Mann Whitney 'U'test
**p < 0.01
*p < 0.025

3. A direct comparison of the activity of Compound (12) and Compound (5) in the croton oil model of topical anti-inflammatory activity A dose response of these Compounds was performed against 1% croton oil in tetrahydrofuran and showed that Compound (12) was of the order of two fold more potent than Compound (5).

| Group | Treated Ear Wt mg ± s.e. | % Inhibition | Untreated Ear Wt mg ± s.e. | % Inhibition |
|---|---|---|---|---|
| Normal control | 98.5 ± 3.0 | — | 99.1 ± 2.6 | — |
| Inflamed control | 126.1 ± 4.0 | — | 118.7 ± 3.3 | — |
| Compound (5) | | | | |
| 4 mg/ear | **108.2 ± 2.8 | 65 | 115.5 ± 5.6 | 16 |
| 2 mg/ear | 116.4 ± 3.8 | 35 | 119.9 ± 5.1 | −6 |
| 1 mg/ear | 124.5 ± 4.6 | 6 | 119.9 ± 4.7 | −6 |
| Compound (12) | | | | |
| 4 mg/ear | **106.3 ± 3.4 | 72 | 120.6 ± 4.5 | −10 |
| 2 mg/ear | **109.8 ± 3.2 | 59 | 117.0 ± 2.8 | 9 |
| 1 mg/ear | 116.1 ± 4.6 | 36 | 112.6 ± 5.5 | 31 |

ED$_{50}$ values
Compound (5) 2.8 mg/ear
Compound (12) 1.6 mg/ear
Significantly different from the inflamed control assessed by the Students 't' test.
**p < 0.01

TOXICITY

No toxic effects were observed in these tests.
What we claim is:
1. A compound of formula:

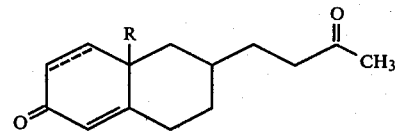

wherein the dotted line is a carbon-carbon single or double bond and R is hydrogen or methyl.

2. 6-(3'-Oxobutyl)-2,3,4,4a,5,6,7,8-octahydronaphthalene-2-one.

3. A pharmaceutical composition having anti-inflammatory activity adapted for topical administration which comprises an anti-inflammatory effective amount of a compound according to claim 1 and a pharmaceutically acceptable carrier.

4. A method of treatment of topical inflammation, which comprises administering to the effected area an effective amount of a compound according to claim 1.

5. A compound selected from the group consisting of

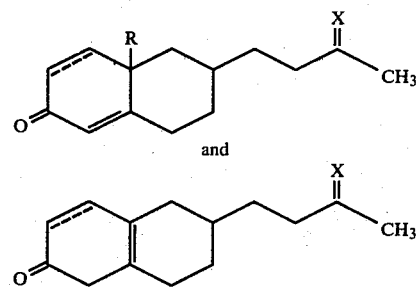

wherein
R is hydrogen or methyl and
X is a ketalized oxo group.

* * * * *